United States Patent [19]

Mahawili

[11] Patent Number: 5,486,207
[45] Date of Patent: Jan. 23, 1996

[54] THERMAL PAD FOR PORTABLE BODY HEATING/COOLING SYSTEM AND METHOD OF USE

[76] Inventor: Imad Mahawili, 1603 Laraway Lake South East, Grand Rapids, Mich. 49546

[21] Appl. No.: 309,360

[22] Filed: Sep. 20, 1994

[51] Int. Cl.⁶ ............................................. A61F 7/00
[52] U.S. Cl. .................................................. 607/104
[58] Field of Search ................. 607/96, 104, 108–112, 607/114

[56] References Cited

U.S. PATENT DOCUMENTS

| | | | |
|---|---|---|---|
| 4,094,357 | 6/1978 | Sgroi | 607/104 X |
| 4,149,541 | 4/1979 | Gammons et al. | 607/104 |
| 4,867,230 | 9/1989 | Voss | 607/108 X |
| 5,106,373 | 4/1992 | Augustine et al. | 607/104 X |

Primary Examiner—Angela D. Sykes
Attorney, Agent, or Firm—John A. Bucher; Robert Charles Hill

[57] ABSTRACT

A thermal pad for use with a portable body heating/cooling system and method of use wherein the system includes a reservoir for hot/cold fluid, supply and return tubes for connecting the reservoir with the pad, pump means for continually circulating fluid between the reservoir and the pad and suitable controls, the thermal pad comprising a single corrugated tube including connectors for connection with the supply and return tubes, the single corrugated tube being folded on itself to form at least parallel passes providing a treatment surface for the pad, a cover extending transversely of the tube passes opposite the treatment surface, strips for securing the ends of the tube passes to the cover and straps for securing the pad in place on the treatment area. Preferably, controls for the thermal pad in combination with the other components of the heating/cooling system include a power supply, a time delay control for selectively establishing respective on and off cycle times and more preferably a battery for portable operation of the system.

22 Claims, 3 Drawing Sheets

5,486,207

THERMAL PAD FOR PORTABLE BODY HEATING/COOLING SYSTEM AND METHOD OF USE

FIELD OF THE INVENTION

The present invention relates to a thermal pad for use with a portable body heating/cooling apparatus and more particularly to specific features of the thermal pad and controls for regulating operation of the thermal pad in combination with other components of the system.

BACKGROUND OF THE INVENTION

The use, of thermal pads for applying hot or cold therapy to different portions of the body has long been recognized as a desirable treatment for a number of conditions. Such treatment has been found helpful in relieving the pain of injuries and arthritis as well as in treating selected body portions such as joints, muscles and the like for sprains, excessive exercise and numerous other conditions.

It is to be noted that the different body portions to be subjected to such treatment include portions of the limbs which can readily be wrapped or encased by a thermal pad as well as substantial, relatively flat portions of the body trunk where the pad must generally be applied in an extended or flat condition.

In treatments of the type summarized above, thermal pads for applying both hot and cold therapy have most commonly relied upon providing a thermal pad which is either hot or cold depending upon the desired treatment. For example, such uses commonly employed heat pads immersed in hot fluid or liquid, electric heat pads, chemical heat pads, cold packs immersed in cold fluid or liquid and direct application of ice to body portions by means of such a thermal pad. These forms of treatment commonly resulted in hot spots, cold spots, cold burns, uncomfortable ice-body contact, moisture on the selected body parts being treated and usually relatively rapid loss of either the hot or cold condition of the pad. Accordingly, it was also necessary to frequently change the pads or to re-immerse them in either hot or cold fluid or liquid.

Improvements in treatment techniques as described above have included the use of improved fasteners such as those available under the VELCRO trade name for securing the pads in place. In addition, although many of the improved systems still employ pads which are themselves either hot or cold, certain prior art systems have been provided for supplying either hot or cold fluid from a separate source. However, these systems were relatively complex. One such system involved the use of an insulated container filled with either hot or cold fluid and connected with heating/cooling units shaped to conform to particular body portions such as the feet or joints. In these prior art systems, fluid from the separate container was allowed to flow to the cuff by gravity and after a selected period of time, the container could be lowered to permit the fluid to flow from the cuff back into the container.

A portable heating/cooling system of the type generally contemplated by the present invention was disclosed in U.S. Pat. No. 5,336,249 issued Aug. 9, 1994 to the inventor of the present invention.

Although these prior art systems and devices were found to be generally adequate for their intended purpose, there has been found to remain a need for further improvements in such systems and methods of use for achieving improved treatment.

SUMMARY OF THE INVENTION

Accordingly, it is an object of the present invention to provide a further improved thermal pad for use with portable body heating/cooling apparatus of the type disclosed above. In this regard, the present invention includes many of the novel features disclosed in the patent noted above. Accordingly, that reference is incorporated as though set forth in its entirety.

In addition, it is also an object of the invention to provide controls for enhancing operation of the thermal pad in combination with other components of the portable body heating/cooling system.

More specifically, it is an object of the present invention to provide a thermal pad for use with a portable body heating/cooling apparatus for thermal treatment of selected body portions, the apparatus including a reservoir, supply and return tubes for interconnection between the reservoir and pad and pump means for continually circulating fluid between the reservoir anti the pad, the thermal pad being formed from a single corrugated tube including means for connection with the supply and return tubes, the single corrugated tube being folded on itself to form multiple parallel passes, at least three passes, providing a treatment surface for the pad, means securing adjacent end portions of the folded tubes, and a cover extending transversely of the tube passes opposite the treatment surface and operatively secured to the outermost tube passes whereby central parallel portions of the tube passes are movably restrained only by the cover in order to permit manipulation of the tube across the treatment surface in order to enhance thermal treatment of various body portions. Preferably, the cover is flexible and wraps around and overlaps a perimeter portion of the outermost tube passes and the folded tube ends in order to movably restrain the tube passes.

It is a further object of the invention to provide straps for securing the pad in place on a selected body portion, the folded tube end portions being preferably secured by means of flexible strips traversing opposite ends of the parallel tube passes, the two strips being secured to the cover respectively intermediate alternate sets of tube passes.

Preferably, the cover is an insulator and the reservoir and supply and return tubes are also insulated to enhance operation of the heating/cooling apparatus.

It is yet another object of the invention to provide controls for the thermal pad in combination with the portable body heating/cooling apparatus, including time delay means for establishing respective on and off cycling times and for causing the pump means to continuously cycle with the established on and off times until termination of the treatment, a power supply for the heating/cooling apparatus preferably comprising a battery in order to make the apparatus fully portable.

Additional objects and advantages of the invention are made apparent in the following description having reference to the accompanying drawings.

DESCRIPTION OF THE PREFERRED EMBODIMENTS

Figure 1:
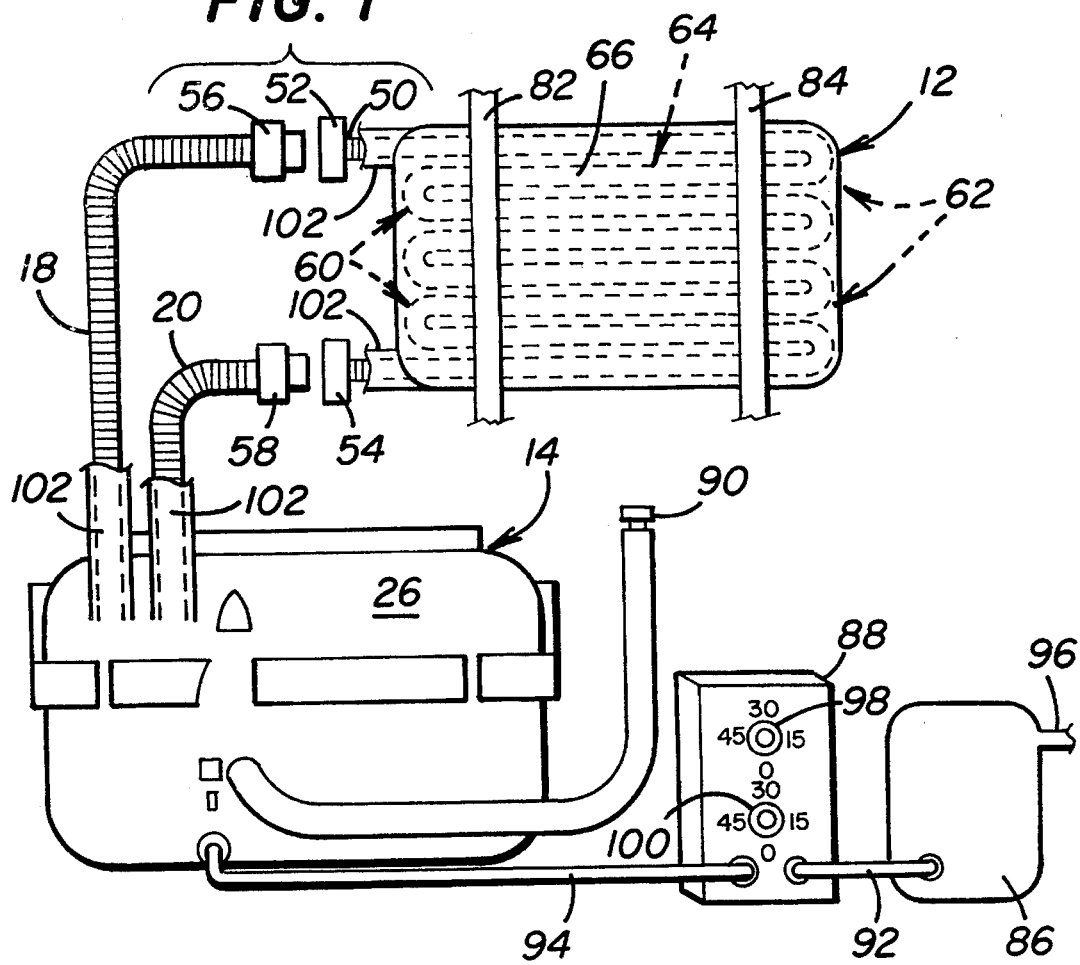
FIG. 1 is view of the covered or back side of the thermal pad in combination with other components of the portable body heating/cooling apparatus.

Referring now to FIG. 1, the present invention provides a portable body heating/cooling apparatus or system generally indicated at 10 for thermal treatment of selected body portions (not shown) such as joints, muscles and the like. Generally, the portable body heating/cooling apparatus 10 is contemplated to include an elongated thermal pad 12 novelly configured as described below for conforming to various body portions and for effectively applying hot or cold therapy thereto.

Figure 2:
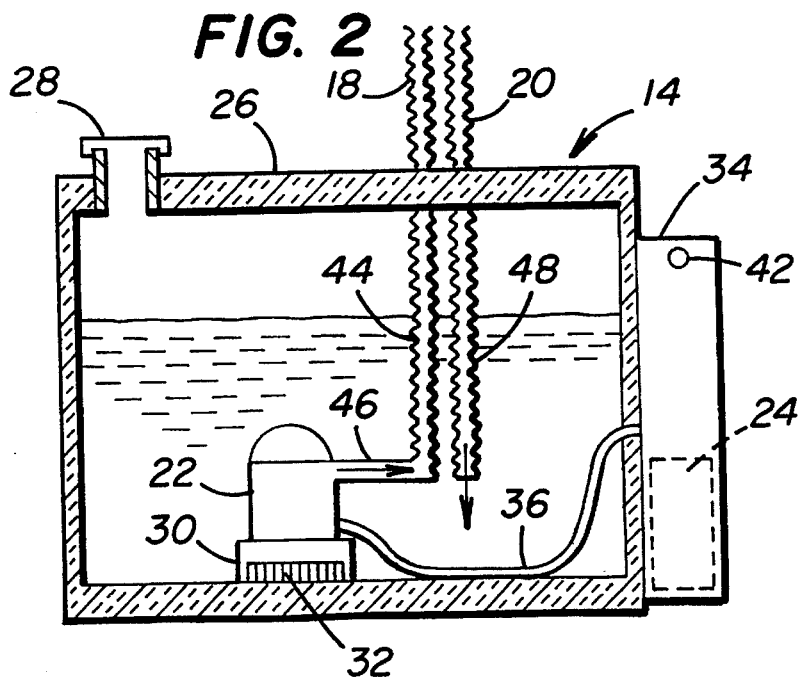
FIG. 2 is a sectioned view of a reservoir for the heating/cooling apparatus

A portable reservoir 14 is connected with the thermal pad by means of non-collapsible supply and return tubes 18 and 20. Referring also to FIG. 2, a pump 22 is provided for continually circulating fluid from the reservoir to the pad through the supply tube 18 and back to the reservoir through the return tube 20. The pump 22 is preferably located within the reservoir 14 and is more preferably operated by a battery 24 in order to further enhance portability and to assure continued circulation of hot/cold fluid through the thermal pad.

The above features of the invention are similar to the present inventor's portable body heating/cooling system described in the patent noted above and are similarly important in the present invention both for gradually applying hot or cold therapy to the selected body portion, that is, at least over a period of several seconds during which fluid from the reservoir either heats or cools the conduit means within the thermal pad. Continued circulation of fluid through the thermal pad by means of the pump 22 assures that the thermal pad remains at generally the same desired temperature for the treatment. At the same time, with the fluid being internally circulated through the pad by the supply and return tubes 18 and 20, direct contact of the fluid with the body is avoided in order to make the therapy more comfortable to the user.

More specific features of the above components are described below in order to more completely disclose the apparatus and method of use for the invention, again similarly to the patent referred to above.

The reservoir 14 is provided with insulated walls or an insulated cover 26 in order to maintain the desired temperature of the hot/cold fluid or liquid over extended periods of time. The reservoir is also provided with access means 28 for adding fluid to the reservoir or removing fluid therefrom. The pump 22 is preferably of a rotary type as illustrated and is operated by a submersible DC marine motor 30 of otherwise conventional construction for achieving high volume pumping of the hot or cold fluid or water being circulated through the thermal pad. A grill 32 provides an inlet to the pump 22 in order to prevent ice entering and interfering with operation of the pump 22 and motor 30.

The reservoir 14 is preferably provided with an accessory panel 34 containing the battery 24. The battery 24 is connected with the motor 30 by means of a waterproof line 36. The reservoir 14 may also be provided with a temperature indicator 42 to indicate the temperature of the fluid or liquid within the reservoir.

The reservoir 14 may also be provided with a temperature indicator 42 to indicate the temperature of the fluid or liquid within the reservoir.

The supply and return tubes 18 and 20 are preferably formed with an accordion-like configuration in order to make them non-collapsible and to better assure continued circulation of fluid from the reservoir through the conduit means 16 and back to the reservoir. Within the reservoir, a tubular extension 44 connects the supply tube 18 with an outlet 46 for the pump 22. Similarly, a tubular extension 48 interconnects the return tube to the reservoir, preferably below the level of fluid in the reservoir.

Both the supply and return tubes 18 and 20 as well as their extensions 44 and 48 within the reservoir are preferably formed from polypropylene corrugated tubing which is both light weight and flexible. Preferably, the tubes are all of about 0.5 inch minimum internal diameter in order to minimize back pressure resistance to the high flow marine DC pump 22. Even larger sizes of tubing could accordingly be used for that purpose. However, the specific size of tubing is not a limiting feature of the invention.

As indicated above, the design of the thermal pad 12 is of particular importance to the present invention and is described below with particular reference to FIGS. 3–5. Initially, the thermal pad is formed from a single corrugated tube 50 including connectors 52 and 54 at its opposite ends for interconnection with connectors 56 and 58 respectively on the conduits 18 and 20. The single corrugated tube is similar to the tubing described in the above noted patent and includes substantially all of the tubing characteristics described in that patent in order to achieve similarly desirable results herein.

In addition, it is important within the present invention that the single tube 50 is formed with a number of turns indicated respectively at opposite longitudinal ends of the pad 12 at 60 and 62. The turns 60 and 62 are arranged to form a multiplicity, at least three and preferably more parallel passes of tubing as generally indicated at 64. The parallel tube passes 64 are secured in place on a cover 66 by means of elongated strips extending transversely of the parallel tube passes respectively adjacent the tube turns 60 and 62 and indicated at 68 and 70. The elongated strips 68 and 70 are preferably formed from elastic fabric and are arranged on an opposite surface of the parallel tube passes 64 from the cover 66. The elongated strips 68 and 70 are attached, for example, by sewing, to the cover intermediate alternate sets of tube passes. More specifically, the strip 68 is secured to the cover at locations collectively indicated at 72 while the other strip 70 is similarly secured to the cover at location 74. Each adjacent pair of connecting locations 72 and 74 span two parallel tube passes adjacent the respective tube turns. Furthermore, the securing locations 72 and 74 are offset with respect to each other as best illustrated in FIG. 4.

Figure 6:
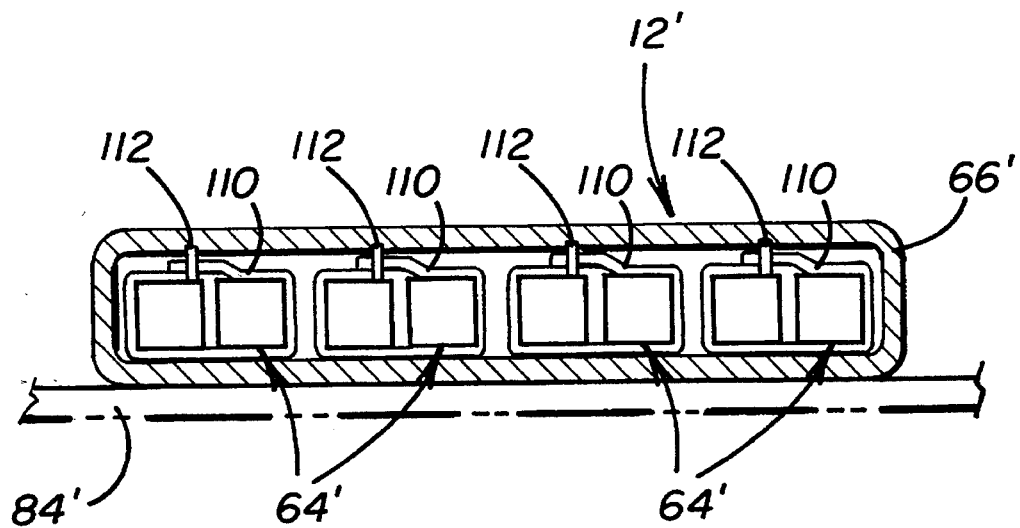
FIG. 6 is a view taken along section line VI—VI in FIG. 3 to illustrate another embodiment of the invention.

Another embodiment of the invention is illustrated in FIG. 6.

Generally, components of the thermal pad of FIG. 6 correspond to elements described above in connection with FIG. 1–5. Accordingly, the thermal pad of FIG. 6 is indicated at 12' and other portions of the thermal pad corresponding to portions of the thermal pad 12 described in FIGS. 1–5 are indicated by similar primed numerals.

Figure 3:
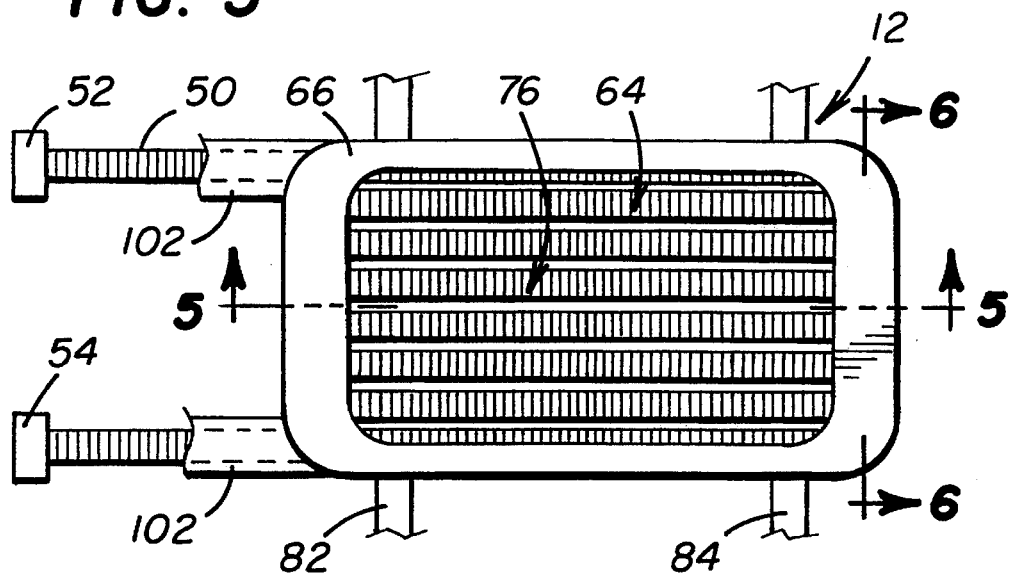
FIG. 3 is a plan view of a treatment surface of the heating pad.
Figure 4:
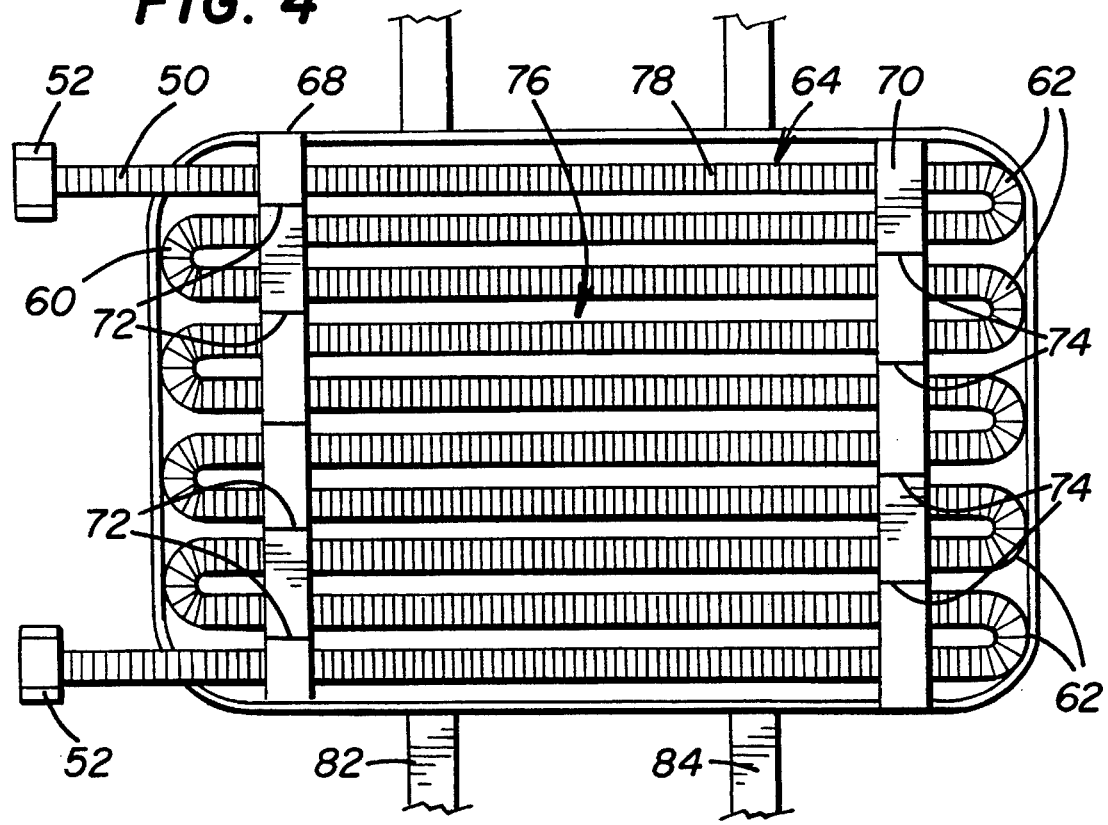
FIG. 4 is a similar view of the heating pad with portions of the cover removed in order to illustrate strips for securing together end portions of the tube passes in the pad.
Figure 5:
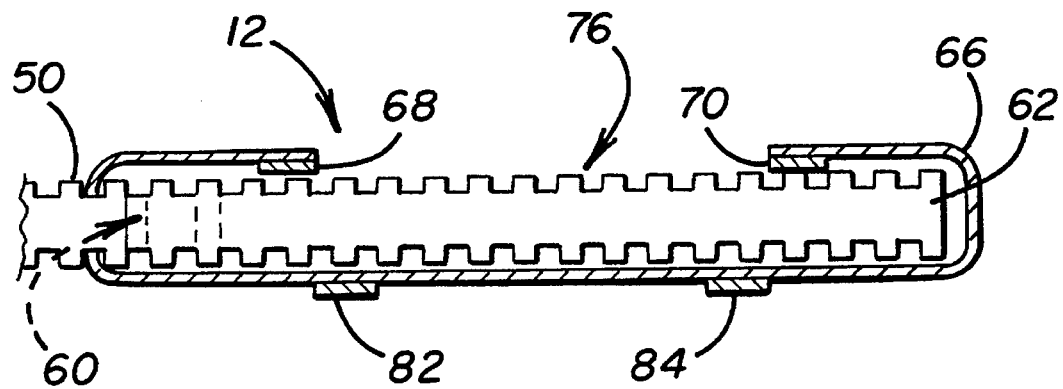
FIG. 5 is a view taken along section line V—V in FIG. 3.

In particular, referring to FIG. 6, the elongated strips 68 and 70 interconnected to the cover between alternate sets of tube passes are respectively replaced by multiple plastic ties 110 similarly arranged adjacent end portions of the parallel tube passes as the strips 68 and 70 of FIGS. 3–5. The plastic ties respectively encircle adjacent pairs of tube passes and are interconnected as indicated at 112 in a manner well known to those skilled in the art. Generally, the plastic ties employed in the embodiment of FIG. 6 are relatively stronger than the elongated strips 68 and 70. Otherwise, the thermal pad 12' of FIG. 6 is substantially similar to the thermal pad 12 described above in connection with FIGS. 3–5.

Referring again to the thermal pad 12 of FIGS. 3–5, the parallel tube passes 64 being arranged collectively as illustrated in FIGS. 3 and 4, one surface of the tube passes is exposed in order to form a treatment surface 76 as illustrated in both FIGS. 3 and 4. Referring momentarily also to FIG. 1, the cover 66 is preferably flexible and may be formed from a cloth material such as canvas, plastic such as nylon, etc. and extends transversely over an opposite surface of the parallel tube passes 64 from the treatment surface 76. As illustrated in FIGS. 3 and 4, the cover is wrapped around the outermost tube passes 78 and 80 as well as the turns 60 and 62 forming the longitudinal ends of the pad 12. The cover is effectively secured to the outermost tube passes 78 and 80 in this manner in order to provide movable restraint for the central parallel tube passes collectively indicated at 64.

Movable or yielding restraint for the central parallel tube passes 64 along the treatment surface 76 is particularly important in order to permit manipulation of the tube passes when the treatment surface 76 of the pad 12 is applied to a body portion to be treated. In this regard, it is further noted that the pad 12 is provided with retaining straps 82 and 84 which are preferably hook and loop type fasteners available for example under the VELCRO trade name. However, other fasteners may also be employed. The VELCRO type fasteners are particularly desirable since they may be employed in engagement with each other to secure the thermal pad 12 when it is wrapped around a body limb for example. On the other hand, the hook and loop configuration of the VELCRO fasteners also permits the straps 82 and 84 to assist in securing or locating the thermal pad 12, for example, by engagement with clothing or the like.

In any event, when the treatment surface 76 of the thermal pad 12 is applied to a selected body portion, the movable restraint for the central parallel tube portions allows for freedom of lateral motion of the tubes prior to tightening of the retaining straps 82 and 84. This is important in order to permit arrangement of the tubes, for example, to avoid direct contact of the tubes with incisions, bruises or the like while still permitting effective thermal treatment of the area.

The thermal pad may of course be formed in a large variety of dimensions depending upon the specific body portion or type of body portions to be treated. In this regard, it is noted that the thermal pads 12 are indicated with a smaller number of parallel tube passes 64 than in FIG. 4. This is merely illustrative of the possibility for changing dimensions, both length and width of the thermal pad of the present invention, for example by increasing or decreasing the number of parallel tube passes, increasing the length of the respective passes or even employing corrugated tubing of different sizes. In addition, the treatment surface 76 of the pad may be formed with a range of tube passes, for example, 4, 6, 8, 10 or even more depending upon the size of the treatment surface 76 for the pad 12.

Additional features of the heating/cooling apparatus are described below with reference also to FIG. 1. Referring particularly to FIG. 1, a power supply 86 is provided for employing line power to either operate the pump 22 and/or to charge the battery 24. Accordingly, the power supply 86 may be uncoupled from the heating/cooling apparatus if desired for increased portability of the unit. Preferably, the power supply 86 is coupled with the motor 30 for the pump 22 and with the battery 24 in series with a time delay controller 88. An on-off switch control is also provided as indicated at 90. Preferably, the power supply 86 is coupled with the time delay controller 88 by a removable coupling 92 and the time delay controller 88 is similarly coupled with the motor 30 and battery 24 by a removable coupling 94. Accordingly, the power supply 86 may be uncoupled either alone or in combination with the time delay controller 88 if desired. In addition to the removable coupling 92, the power supply 86 is also provided another conduit 96 for coupling into a receptacle to receive line power.

With the above configuration, the heating/cooling apparatus may be simply operated by the on-off switch 90. However, in many if not most applications, patients prefer to choose the duration of on and off times either subjectively or otherwise. For that reason, the time delay controller includes separate controls 98 and 100 for respectively determining cycled on and off time. With suitable on and off times being established by the controls 98 and 100, operation of the motor 30 is cycled on and off accordingly ad infinitum until operation of the apparatus is terminated by the switch 90.

As noted above, the cover 66 is preferably relatively thick or otherwise provided with insulating value in order to enhance thermal effects at the exposed treatment surface 76. For similar reasons, the reservoir 14 is also preferably insulated as noted above. In addition, insulated sleeves 102 are preferably provided for the conduits 18 and 20 as well as the two exposed ends of the single corrugated tube 50. Accordingly, thermal treatment is further enhanced in this regard and handling of the heating/cooling apparatus is also facilitated.

Accordingly, there has been described above a novel thermal pad for use with heating/cooling apparatus as described above and novel components in the heating/cooling apparatus to further facilitate thermal treatment. A method of use for the heating/cooling apparatus and particularly for the thermal pad 12 is believed apparent from the preceding description. However, the method of use is briefly described below in order to assure a complete understanding of the invention.

Initially, the reservoir 14 is filled with a suitable fluid, usually hot water or ice water depending upon the particular therapy desired. It would also of course be possible to employ either heating or cooling apparatus within the reservoir 14. However, this would tend to complicate the apparatus and reduce its portability. In any event, the thermal pad 12, configured as described above, is interconnected with the reservoir by the supply and return tubes 18 and 20 and is then applied to a selected portion of the body to receive hot or cold therapy.

The thermal pad 12 is positioned with the treatment surface 76 and the array of parallel tube passes 64 arranged over and in contact with the body portion to be treated. As the thermal pad 12 is applied to the selected body portion, the movably restrained central portions of the parallel tube passes may readily be manipulated as described above in order to enhance effectiveness of the heating/cooling apparatus and also possibly to make the patient more comfortable during the treatment. With the central portions of the parallel tube passes manipulated in this manner, the thermal pad 12 is then secured in place over the selected body portion by the retaining straps 82 and 84.

With the thermal pad 12 in place, operation of the pump 24 is initiated by the motor 30 and controls including either the battery 26 or the power supply 86 in combination with the time delay controller 88. In this manner, the motor 30 is caused to operate the pump 24 for supplying hot or cold fluid from the reservoir to circulate through the parallel tube passes 64 of the thermal pad 12 by means of the supply and return tubes 18 and 20. Particularly because of the corrugated configuration of the tube 50, circulation of the fluid causes the temperature of the thermal pad 12 to be increased or decreased relatively gradually at least over a few seconds, in order to minimize thermal shock to the body portion being treated. Fluid is then continually circulated through the conduit means of the thermal pad in order to maintain a generally uniform therapy temperature on the selected body portion. However, it is noted again that the time delay controller 88 is preferably employed to selectively cycle operation of the motor 30 and pump 22 between on and off conditions as selected by the patient or user of the apparatus as noted above. However, if desired, the apparatus could also be employed to continuously heat or cool the selected body portion. In any event, the therapy may then be continued for any desired length of time and then terminated by the switch 90.

The apparatus and method of use described above make various modifications or additions obvious. However, other modifications and additions are believed apparent from the description. Accordingly, the scope of the present invention is defined only by the following claims which are further exemplary of the invention.

What is claimed is:

1. A thermal pad for use with a portable body heating/cooling apparatus for thermal treatment of selected body portions including a reservoir, supply and return tubes for interconnection between the reservoir and pad and pump means for continually circulating fluid from the reservoir to the pad and back, the thermal pad comprising a single corrugated tube including means for connection with the supply and return tubes, the single corrugated tube being folded on itself to form at least three parallel passes providing a treatment surface for the pad, said at least three parallel passes having outermost tube passes, means securing adjacent end portions of the folded tubes, and a cover extending transversely of the parallel passes opposite the treatment surface and operatively secured to the outermost tube passes whereby central parallel portions of the passes are movably restrained only by the cover in order to permit manipulation of the passes across the treatment surface.

2. The thermal pad of claim 1 further comprising straps attached to the cover for securing the pad in place over a selected body portion with the treatment surface facing the body portion and the tube passes positioned to facilitate comfortable and effective thermal treatment.

3. The thermal pad of claim 1 wherein the securing means comprises two flexible strips traversing opposite ends of the parallel tube passes, the two strips being secured to the cover respectively intermediate alternate sets of tube passes.

4. The thermal pad of claim 1 wherein the securing means comprises a plurality of plastic ties traversing opposite ends of the parallel tube passes, each plastic tie secured together to adjacent tube passes.

5. The thermal pad of claim 1 wherein the cover has substantial insulating value to facilitate manipulation of the pad and to enhance desired thermal effects on the treatment surface of the pad.

6. The thermal pad of claim 5 wherein the cover is cloth peripherally overlapping the outermost tube passes and folded tube ends about the perimeter of the thermal pad for movably restraining the central parallel portions of the tube passes.

7. The thermal pad of claim 1 in combination with the reservoir, supply and return tubes and pump means and further comprising power supply means for the pump means.

8. The thermal pad of claim 7 further comprising an adjustable time delay means for establishing respective on and off times and for causing the pump means to continuously cycle with the established on and off times until termination of the treatment.

9. The thermal pad of claim 8 further comprising an on-off control for selectively initiating and terminating treatment.

10. The thermal pad of claim 8 further comprising straps attached to the cover for securing the pad in place over a selected body portion with the treatment surface facing the body portion and the tube passes positioned to facilitate comfortable and effective thermal treatment.

11. The thermal pad of claim 8 wherein the securing means comprises two flexible strips traversing opposite ends of the parallel tube passes, the two strips being secured to the cover respectively intermediate alternate tube passes.

12. The thermal pad of claim 8 wherein the cover has substantial insulating value to facilitate manipulation of the pad and to enhance desired thermal effects on the treatment surface of the pad.

13. The thermal pad of claim 8 further comprising straps attached to the cover for securing the pad in place over a selected body portion with the treatment surface facing the body portion and the tube passes positioned to facilitate comfortable and effective thermal treatment.

14. The thermal pad of claim 8 wherein the power supply means is a battery pack to further enhance portability.

15. In a method employing a portable body heating/cooling system for thermal treatment, the steps comprising storing hot/cold fluid in an insulated reservoir, arranging a thermal pad in thermally conductive relation with a selected body portion to be treated, interconnecting the reservoir and the thermal pad by non-collapsible supply and return tubes, continually pumping the fluid in circulation from the reservoir to the thermal pad and back, and providing the thermal pad with a single corrugated tube including means for connection with the supply and return tubes, folding the single corrugated tube on itself to form at least three parallel passes including outermost tube passes and providing a treatment surface for the pad, securing adjacent end portions of the folded tube, and providing a cover extending transversely of the parallel passes opposite the treatment surface and operatively securing the cover to the outermost tube passes whereby central parallel portions of the passes are movably restrained only by the cover in order to permit manipulation of the passes across the treatment surface.

16. The method of claim 15 further comprising the step of attaching straps to the cover for securing the pad in place over a selected body portion with the treatment surface facing the body portion and the tube passes positioned to facilitate comfortable and effective thermal treatment.

17. The method of claim 15 further comprising the step of securing adjacent end portions of the folded tube by means of two flexible strips traversing opposite ends of the parallel tube passes and securing the two strips to the cover respectively intermediate alternative tube passes.

18. The method of claim 15 further comprising the step of securing adjacent end portions of the folded tube by means of a plurality of plastic ties traversing opposite ends of the parallel tube passes, each plastic tie secured together to adjacent tube passes.

19. The method of claim 15 wherein the cover and the reservoir are insulated to facilitate manipulation of the pad and to enhance desired thermal effects on the treatment surface of the pad.

20. The method of claim 15 wherein the cover is cloth peripherally overlapping the outermost tube passes and folded tube ends about the perimeter of the thermal pad for movably restraining the central parallel portions of the tube passes.

21. The method of claim 15 further comprising the step of operating the pump means from a power supply means through an adjustable time delay means for establishing respective on and off times and for causing the pump means to continuously cycle with the established on and off times until termination of the treatment.

22. The method of claim 15 wherein the power supply comprises a battery pack to further enhance portability.

* * * * *